United States Patent [19]
Jones et al.

[11] Patent Number: 5,663,213
[45] Date of Patent: Sep. 2, 1997

[54] METHOD OF IMPROVING ULTRAVIOLET RADIATION ABSORPTION OF A COMPOSITION

[75] Inventors: Charles Elwood Jones, Yardley; Rafael Gonzalez Aviles, Harleysville; David Michael Fasano, Maple Glen; Martin Vogel, Jenkintown, all of Pa.

[73] Assignee: Rohm and Haas Company, Philadelphia, Pa.

[21] Appl. No.: 518,698

[22] Filed: Aug. 24, 1995

Related U.S. Application Data

[63] Continuation-in-part of Ser. No. 203,178, Feb. 28, 1994, abandoned.

[51] Int. Cl.$^6$ .............................. A61K 7/42; A61K 7/49
[52] U.S. Cl. .................... 523/105; 523/122; 523/201; 514/772.3; 424/60; 424/78.08; 424/419; 424/501; 424/642
[58] Field of Search ..................... 523/105, 122, 523/201; 514/772.3; 424/60, 78.08, 419, 501, 642

[56] References Cited

U.S. PATENT DOCUMENTS

| | | |
|---|---|---|
| 4,427,836 | 1/1984 | Kowalski et al. . |
| 4,468,498 | 8/1984 | Kowalski et al. . |
| 4,469,825 | 9/1984 | Kowalski et al. . |
| 4,594,363 | 6/1986 | Blankenship et al. . |
| 4,677,003 | 6/1987 | Redlich et al. . |
| 5,243,021 | 9/1993 | Langer et al. . |
| 5,505,935 | 4/1996 | Guerrero et al. ............... 424/59 |

FOREIGN PATENT DOCUMENTS

| | | |
|---|---|---|
| 267726 | 3/1991 | European Pat. Off. . |
| 2646346 | 4/1989 | France . |
| 2681248 | 9/1991 | France . |
| 9227813 | 12/1984 | Japan . |
| 130655 | 8/1985 | Japan . |
| 149515 | 8/1985 | Japan . |
| 149516 | 8/1985 | Japan . |
| 149517 | 8/1985 | Japan . |
| 224609 | 11/1985 | Japan . |
| 1037711 | 2/1986 | Japan . |
| 1168528 | 7/1986 | Japan . |

(List continued on next page.)

OTHER PUBLICATIONS

"Formulating Sunscreen Products", Kenneth Kline, Cosmetech Laboratories, Inc., chap. 16, pp. 235–266.
"For Formulation Chemists Only F2CO", E. M. Morsey, vol. 3, pp. 408–411.
"Transparent Tio2 for UV–Protection", Sibylle Tichy, Soew Journal 118 Labratories, Oct. 1992.
"Cosmetics", vol. 7, pp. 152–154.
Sun Products Documentary, "Sunscreen and Suntan Products: Patent and Literature Update", Charles Fox, N.J.
"The Strcture and Function of Skin", K. Laden and C. Felger; Chap. 11, pp. 141–158.
"Some of a body's crucial functions are only skin deep", Albert Rosenfeld, pp. 159–180.
Sun Products Documentary, "Human Sunscreen Evaluation: Protection from Sunburn", Ward L. Billhimer, Hilltop Research, Inc. Ohio.
"A Concise Guide to Topical Sunscreens State of the Art", M. J. Stiller, M.D.; I.C. Davis, M.D., and J.L. Shupack, M.D., International Journal of Dermatology, vol. 31, No. 88, Aug. 1992.
Encyclopedia of UV Absorbers for Sunscreen Products, Ken Klein, Cosmetech Laboratories, Inc., NJ, vol. 1107, Oct. 1992.

*Primary Examiner*—Kriellion S. Morgan
*Attorney, Agent, or Firm*—Kimberly R. Hild

[57] ABSTRACT

A method is disclosed for improving the UV radiation absorption of a composition containing a UV radiation absorbing agent by adding from about 0.1 weight percent to about 50 weight percent of latex particles, based on total weight nonvolatiles. The latex particles contain a void and have a particle size of from about 100 nm to about 380 nm.

7 Claims, 5 Drawing Sheets

FOREIGN PATENT DOCUMENTS

| | | |
|---|---|---|
| 6293220 | 4/1987 | Japan . |
| 3126813 | 5/1988 | Japan . |
| 1014877 | 10/1988 | Japan . |
| 2198612 | 9/1989 | Japan . |
| 2091109 | 3/1990 | Japan . |
| 4009319 | 1/1992 | Japan . |
| 2170105 | 7/1986 | United Kingdom . |
| 8801164 | 2/1988 | WIPO . | ns:

METHOD OF IMPROVING ULTRAVIOLET RADIATION ABSORPTION OF A COMPOSITION

This is a continuation-in-part of application Ser. No. 08/203,178 filed on Feb. 28, 1994, abn.

FIELD OF THE INVENTION

This invention relates to a method of improving absorption of ultraviolet radiation by adding voided latex particles to a composition containing at least one ultraviolet radiation absorbing agent.

BACKGROUND OF THE INVENTION

Six percent of the solar energy reaching the earth's surface is ultraviolet (UV) radiation having a wavelength of 290–400 nanometers (nm). This radiation has two components:

(1) 5.5% UVA having a wavelength of 320–400 nm and
(2) 0.5% UVB having a wavelength of 290–320 nm.

While the UV portion of the solar energy is relatively small, it induces nearly 99% of all the side effects of sunlight. UVB radiation, for example, is responsible for producing sunburn, aging and cancer of the skin. UVA radiation, for example, causes direct tanning and erythema (abnormal redness) and contributes to aging of the skin.

By avoiding exposure to sunlight, people can avoid the serious effects caused by the UV radiation. However, because of the nature of their work, some people cannot avoid exposure to the sun. In addition, others voluntarily expose their skin to the sun to tan, sometimes to extremes. Therefore, protection against the harmful effects of the sun is important.

Protection from these harmful effects of UV radiation exposure is available in the form of both topically applied formulations containing at least one physical blocker, or at least one chemical absorber, or combinations thereof. Physical blockers include active ingredients such as red petrolatum, titanium dioxide and zinc oxide. Chemical absorbers include active ingredients, such as para-aminobenzoic acid (more commonly known as PABA), which are generally transparent when applied and act by absorbing UV radiation, offering selective protection against certain UV wave bands, depending upon the absorption spectrum of the particular active ingredient incorporated into the formulation.

The effectiveness of a sunscreen formulation is generally assessed by how well it protects the skin in terms of a Sun Protection Factor (SPF) which is defined as the ratio of the amount of energy required to produce a minimal erythema on sunscreen protected skin to the amount of energy required to produce the same level of erythema on unprotected skin.

A number of the chemical absorbers and physical blockers, herein after referred to as "UV radiation absorbing agents," typically used in sunscreen formulations have adverse toxicological effects. Therefore, it is desirable to reduce the level of UV radiation absorbing agents present in a sunscreen formulation without reducing the level of protection.

One attempt to reduce the level of UV radiation absorbing agents in a sunscreen formulation is disclosed in U.S. Pat. No. 4,804,531 to Grollier, hereinafter referred to as "Grollier." Grollier discloses adding to a cosmetic screening composition an aqueous dispersion of water insoluble polymer particles where the polymer particles comprise a) an ionic polymer forming a core capable of being swollen, and b) a polymer forming a sheath at least partially encapsulating the core. The water insoluble polymer particles are disclosed to be film forming, to have a sheath glass transition temperature below 50° C., and to have an average particle size before swelling of from 70 nanometers (nm) to 4500 nm. Grollier discloses that when the water insoluble polymer particles are added to a cosmetic screening composition at a level of from 0.1 to 10 weight percent, based on the total weight of the cosmetic screening composition, the absorption of UV radiation in the cosmetic screening composition is increased.

Improving upon the teachings of Grollier, we have unexpectedly found that voided latex particles having certain particle sizes, increase the absorbance of UV radiation in a composition containing one or more UV radiation absorbing agents.

SUMMARY OF THE INVENTION

We have discovered a method for improving UV radiation absorption of a composition, comprising: adding to said composition from about 0.1 weight percent to about 50 weight percent of latex particles, based on total weight of nonvolatiles, wherein the composition comprises at least one UV radiation absorbing agent, and wherein the latex particles contain a void and have a particle size of from about 100 nm to about 380 nm.

DETAILED DESCRIPTION OF THE INVENTION

Figure 1:
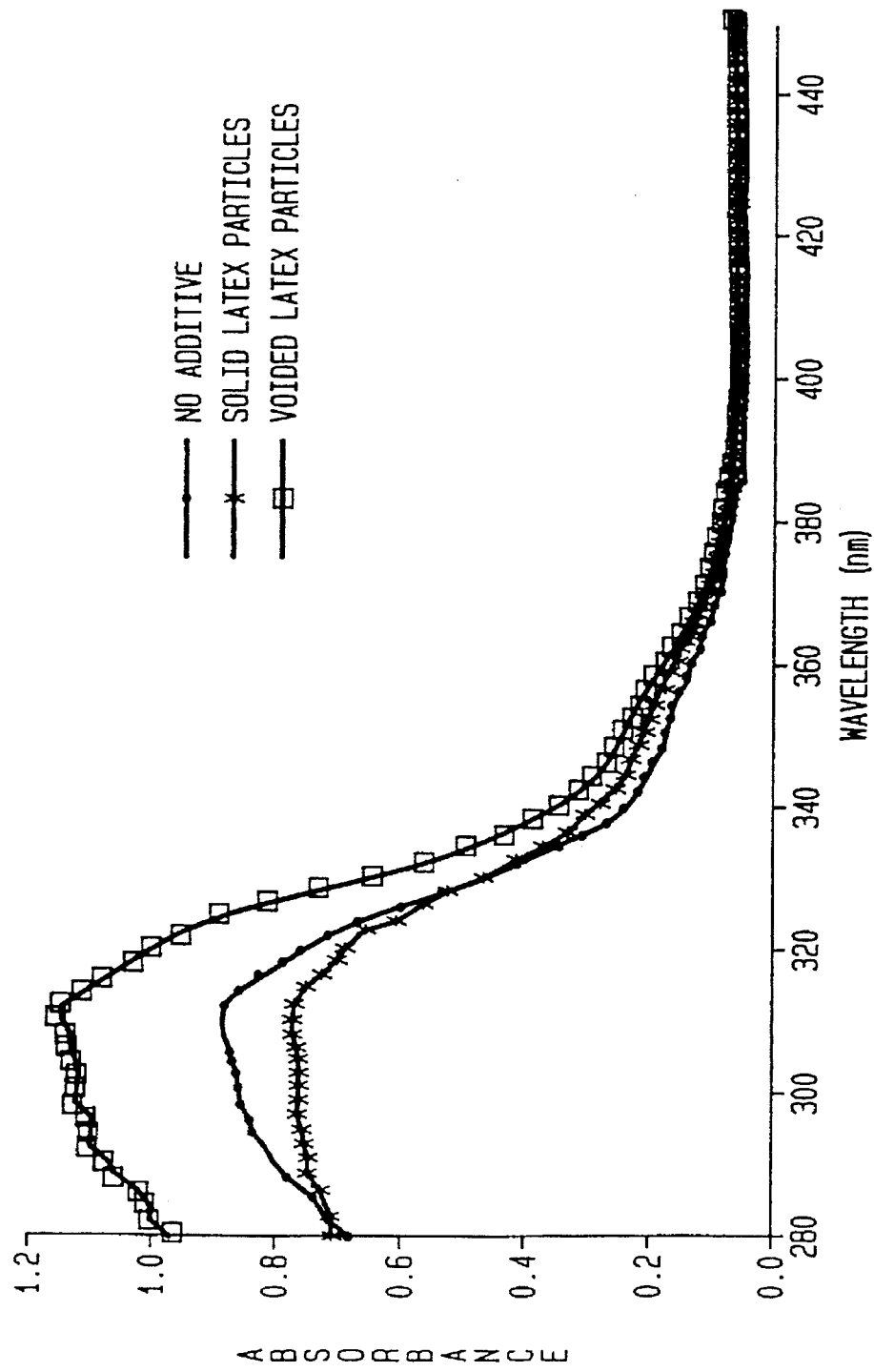
FIG. 1 is a UV radiation absorbance spectrum from a wavelength of 280–440 nm for compositions containing no additives, solid latex particles and voided latex particles at a coating level of 5 microliters per square inch ($\mu l/in^2$). The active ingredients in the compositions are 2-ethylhexyl para-methoxycinnamate and menthyl anthranilate. The additives are incorporated at a level of 5% by weight, based on total weight nonvolatiles.
Figure 2:
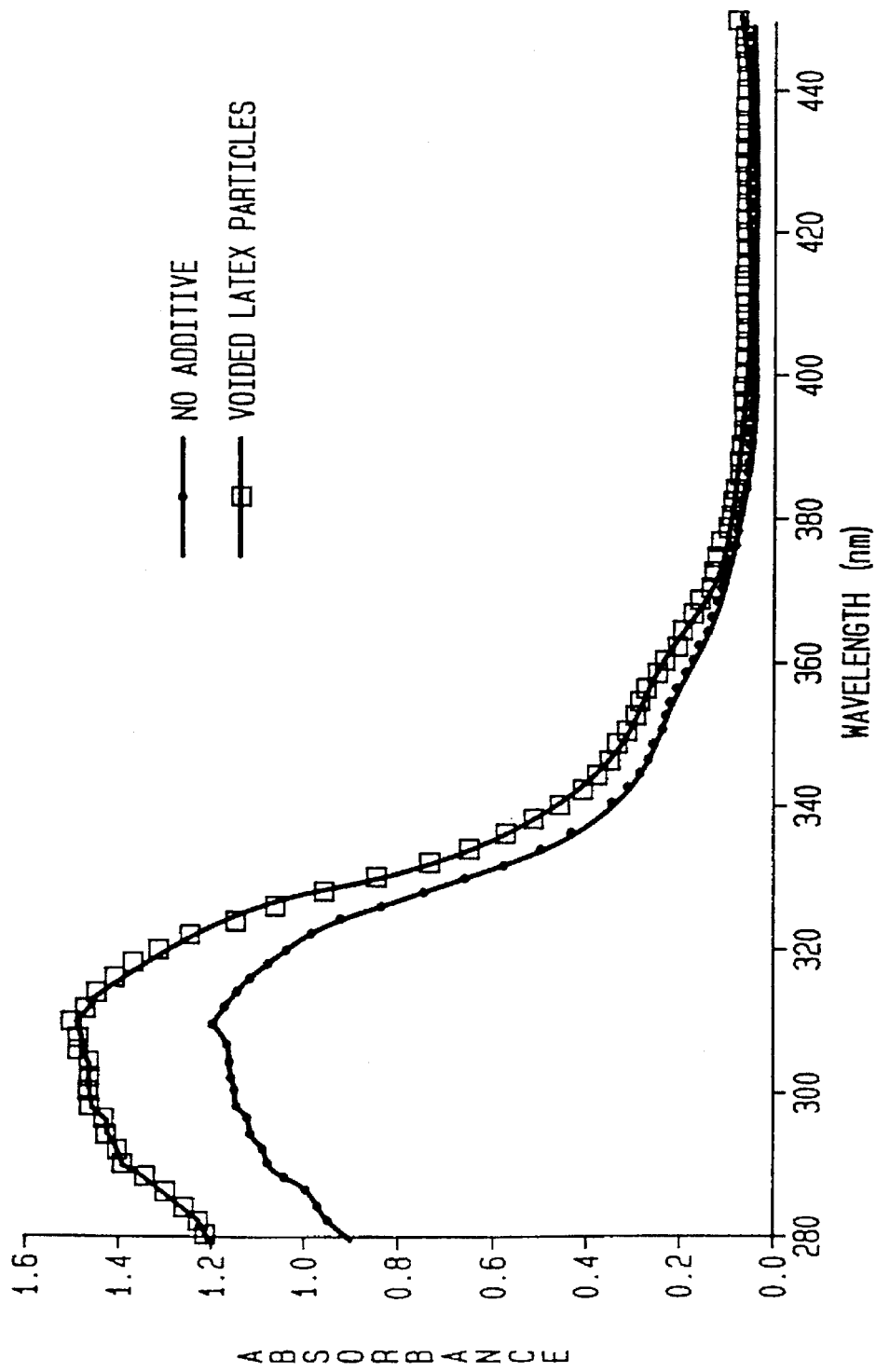
FIG. 2 is a UV radiation absorbance spectrum from a wavelength of 280–440 nm for compositions containing no additives and voided latex particles at a coating level of 10 $\mu l/in^2$. The active ingredients in the compositions are 2-ethylhexyl para-methoxycinnamate and menthyl anthranilate. The additives are incorporated at a level of 5% by weight, based on total weight nonvolatiles.
Figure 3:
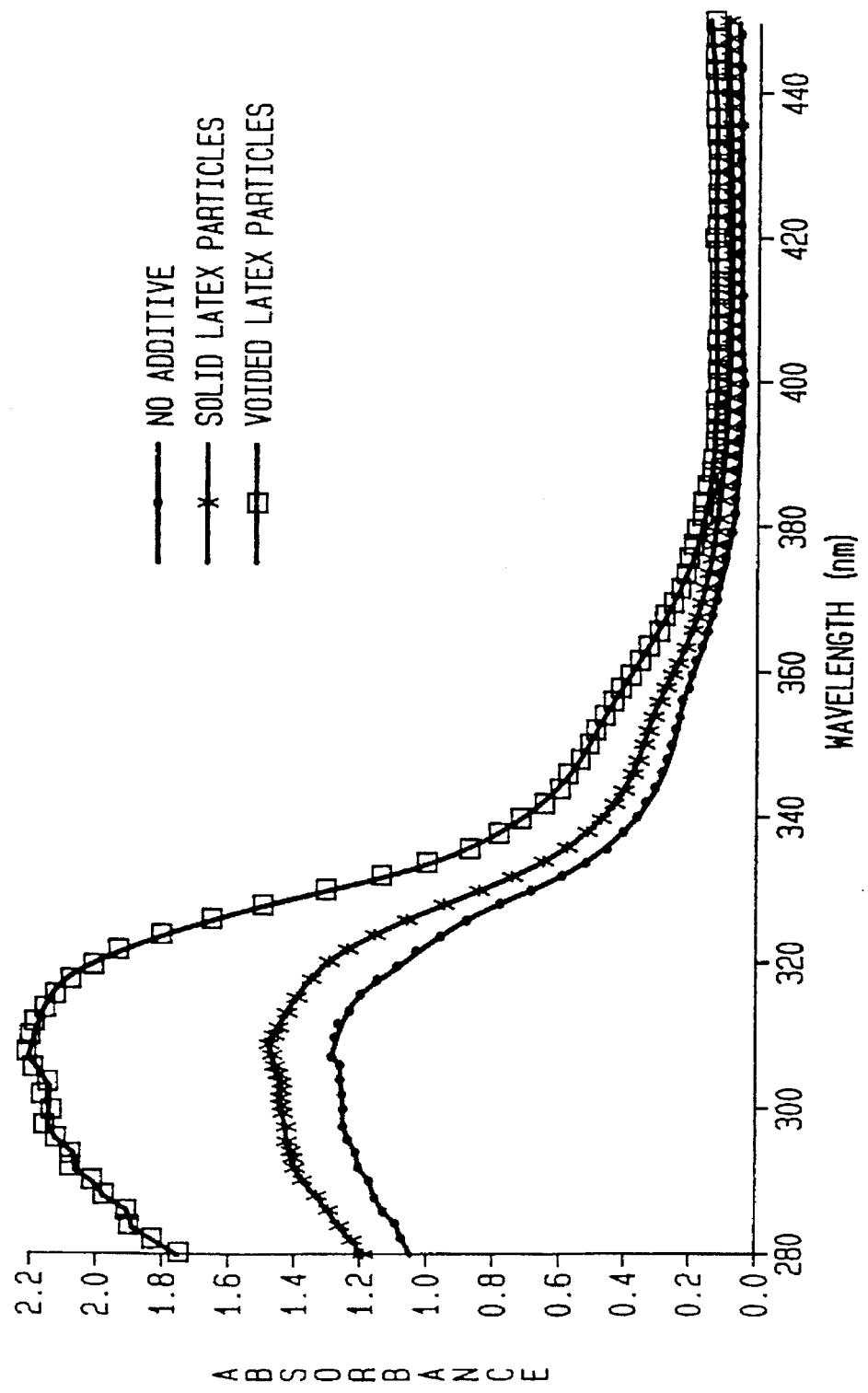
FIG. 3 is a UV radiation absorbance spectrum from a wavelength of 280–440 nm for compositions containing no additives, solid latex particles and voided latex particles at a coating level of 20 $\mu l/in^2$. The active ingredients in the compositions are 2-ethylhexyl para-methoxycinnamate and menthyl anthranilate. The additives are incorporated at a level of 5% by weight, based on total weight nonvolatiles.
Figure 4:
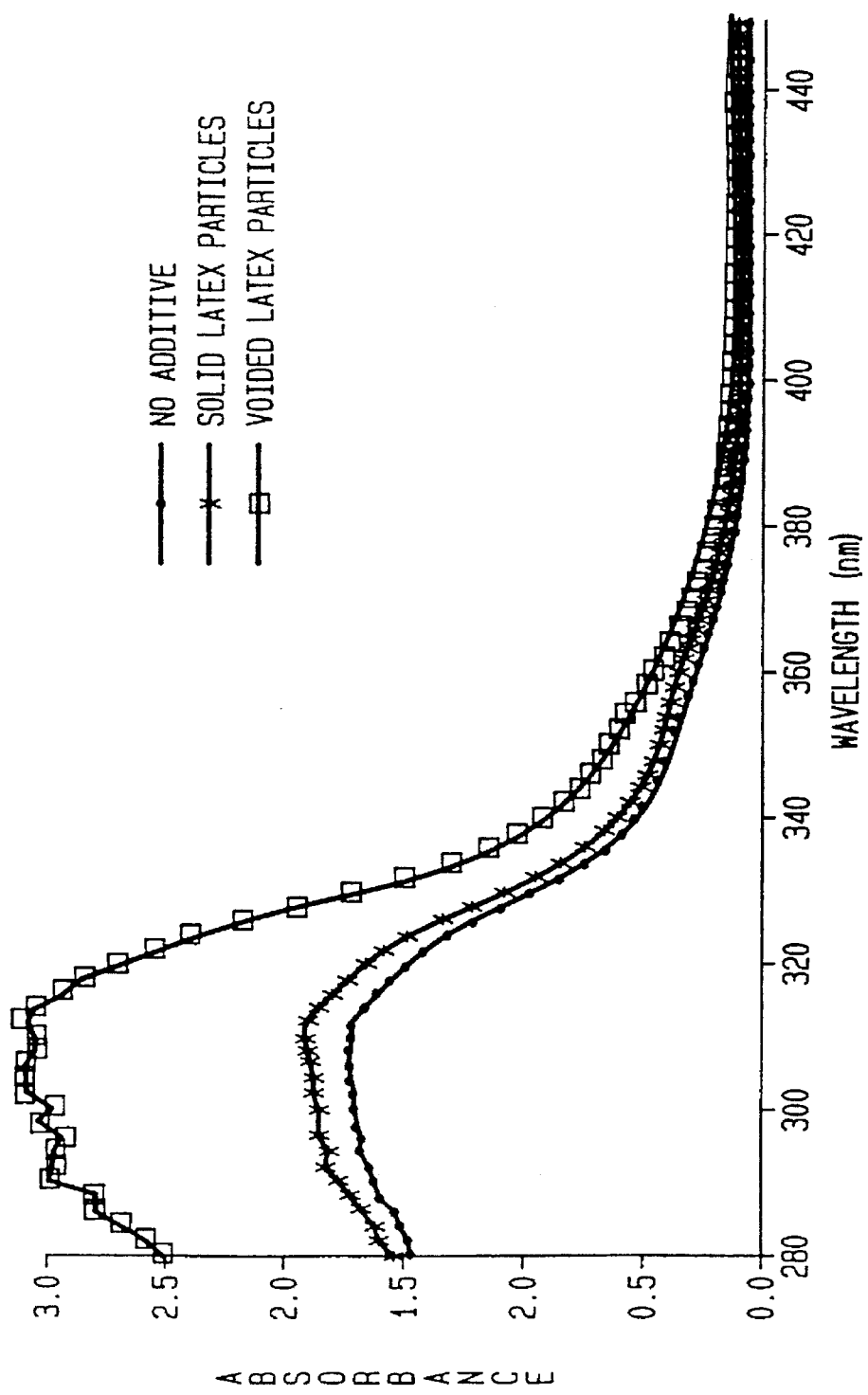
FIG. 4 is a UV radiation absorbance spectrum from a wavelength of 280–440 nm for compositions containing no additives, solid latex particles and voided latex particles at a coating level of 40 $\mu l/in^2$. The active ingredients in the compositions are 2-ethylhexyl para-methoxycinnamate and menthyl anthranilate. The additives are incorporated at a level of 5% by weight, based on total weight nonvolatiles.

The method of the invention improves the UV radiation absorption of a composition containing at least one UV radiation absorbing agent. The method of the present invention includes incorporating from about 0.1 weight percent to about 50 weight percent, and preferably from about 1 weight percent to about 20 weight percent, based on total weight nonvolatiles, of voided latex particles to a composition containing at least one ultraviolet radiation absorbing agent. As used herein, the term "UV radiation" includes both UVA and UVB radiation.

The latex particles useful in the method of this invention have a particle size of from about 100 nanometers (nm) to about 380 nm, preferably from about 150 nm to about 375 nm, more preferably from about 190 nm to about 350 nm, and most preferably from about 251 nm to about 325 nm as measured by a Brookhaven BI-90 photon correlation spectrometer.

For a given particle size, it is desirable to produce latex particles with a maximum void fraction as current processing techniques and particle integrity will permit. Preferably, the latex particles contain a void with a void fraction of from about 0.1% to about 50%, and more preferably from about 5% to about 50%. The void fractions are determined by comparing the volume occupied by the latex particles after they have been compacted from a dilute dispersion in a centrifuge to the volume of non-voided particles of the same composition.

The voided latex particles useful in the method of this invention are formed from a multistaged particle comprising at least one core polymer and at least one shell polymer. The core polymer and shell polymer may be made in a single polymerization step or in a sequence of polymerization steps.

The voided latex particles are prepared by conventional polymerization techniques such as, sequential emulsion polymerization, including those processes disclosed in U.S. Pat. Nos. 4,427,836; 4,469,825; 4,594,363; 4,677,003; 4,920,160; 4,970,241, whose disclosures are incorporated herein by reference. The voided latex particles may also be prepared, for example, by polymerization techniques disclosed in European Patent Application 0,267,726, European Patent Application 0,331,421, U.S. Pat. No. 4,910,229, or U.S. Pat. No. 5,157,084.

The monomers used in the emulsion polymerization of the shell polymer of the voided latex particles preferably comprise one or more non-ionic ethylenically unsaturated monomer. Optionally, one or more monoethylenically unsaturated monomers containing at least one carboxylic acid group may be polymerized in the shell.

The monomers which comprise the shell are selected to provide a glass transition temperature (Tg) in at least one shell which is high enough to support the void within the latex particle. Preferably the Tg of at least one shell is greater than 50° C., more preferably greater than 60° C., and most preferably greater than 70° C. as measured by differential scanning calorimetry.

The monomers used in the emulsion polymerization of the core polymer of the voided latex particles preferably comprise one or more monoethylenically unsaturated monomers containing at least one carboxylic acid group. Preferably, the core comprises at least 5 weight percent of the monoethylenically unsaturated monomers containing at least one carboxylic acid, based on total monomer weight of the core. The core polymer may be obtained, for example, by the emulsion homopolymerization of the monoethylenically unsaturated monomer containing at least one carboxylic acid group or by copolymerization of two or more of the monoethylenically unsaturated monomers containing at least one carboxylic acid group. Preferably, the monoethylenically unsaturated monomer containing at least one carboxylic acid group is copolymerized with one or more non-ionic (that is, having no ionizable group) ethylenically unsaturated monomers.

The core polymer or shell polymer may optionally contain from about 0.1 weight percent to about 20 weight percent, preferably about 0.1 weight percent to about 3 weight percent, based on the total monomer weight of the core, of polyethylenically unsaturated monomer, such as ethylene glycol di(meth)acrylate, allyl(meth)acrylate, 1,3-butanediol di(meth)acrylate, diethylene glycol di(meth)acrylate, trimethylolpropane tri(meth)acrylate, or divinylbenzene. Alternatively, the core polymer or shell polymer may optionally contain from about 0.1 weight percent to about 60 weight percent, based on the total monomer weight of the core, of butadiene.

Suitable monoethylenically unsaturated monomers containing at least one carboxylic acid group include for example acrylic acid and methacrylic acid, acryloxypropionic acid, (meth)acryloxypropionic acid, itaconic acid, aconitic acid, maleic acid or anhydride, fumaric acid, crotonic acid, monomethyl maleate, monomethyl fumarate, and monomethyl itaconate. Acrylic acid and methacrylic acid are preferred.

Suitable non-ionic ethylenically unsaturated monomers include for example styrene, vinyltoluene, ethylene, vinyl acetate, vinyl chloride, vinylidene chloride, acrylonitrile, (meth)acrylamide, ($C_1$–$C_{20}$) alkyl or ($C_3$–$C_{20}$) alkenyl esters of (meth)acrylic acid, such as methyl (meth)acrylate, ethyl (meth)acrylate, butyl (meth)acrylate, 2-ethylhexyl (meth) acrylate, benzyl (meth)acrylate, lauryl (meth)acrylate, oleyl (meth)acrylate, palmityl (meth)acrylate and stearyl (meth) acrylate. As used herein, the term "(meth)acrylic" is intended to serve as a generic expression embracing both acrylic and methacrylic.

The void of the latex particles is preferably produced by swelling the core with a swelling agent containing one or more volatile components. The swelling agent permeates the shell to swell the core. The volatile components of the swelling agent can then be removed by drying the latex particles, causing a void to be formed within the latex particles. Preferably, the swelling agent is an aqueous base. The aqueous base useful for swelling the core includes, for example, ammonia, ammonium hydroxide, alkali metal hydroxides, such as sodium hydroxide, or a volatile amine such as trimethylamine or triethylamine.

The voided latex particles may be added to the composition with the swelling agent present in the core. When the latex particles are added to the composition with the swelling agent present in the core, the volatile components of the swelling agent will be removed upon drying of the composition. The voided latex particles may also be added to the composition after removing the volatile components of the swelling agent.

In addition to the voided latex particles, the composition improved by the method of the present invention contains at least one UV radiation absorbing agent. The UV radiation absorbing agent may be incorporated into the composition at a level to produce a desired sun protection factor. For example, the UV radiation absorbing agent may be added to the composition at a level of generally from about 0.1 weight percent to about 15 weight percent, based on the total weight of nonvolatiles in the composition.

The UV absorbing agents used in the method of this invention are conventional materials. Suitable UV radiation absorbing agents include, for example, oxybenzone, dioxybenzone, sulisobenzone, menthyl anthranilate, para-aminobenzoic acid, amyl para-dimethylaminobenzoic acid, octyl para-dimethylaminobenzoate, ethyl 4-bis (hydroxypropyl) para-aminobenzoate, polyethylene glycol (PEG-25) para-aminobenzoate, ethyl 4-bis(hydroxypropyl) aminobenzoate, diethanolamine para-methyoxycinnamate, 2-ethoxyethyl para-methoxycinnamate, ethylhexyl para-methoxycinnamate, octyl paramethoxycinnamate, isoamyl para-methoxycinnamate, 2-ethylhexyl 2-cyano-3,3-diphenyl-acrylate, 2-ethylhexyl salicylate, homomenthyl salicylate, glyceryl aminobenzoate, triethanolamine salicylate, digalloyl trioleate, lawsone with dihydroxyacetone, 2-phenylbenzimidazole-5-sulfonic acid, benzylidine camphor, avobenzone, titanium dioxide, and zinc oxide.

The composition improved by the method of this invention may also include other conventional ingredients used in UV absorbing compositions. For example, if the composition is used as a sunscreen, it may additionally include water, film forming materials, emulsifiers, water, emollients, water-proofing agents, oils, stabilizers, thickeners, preservatives, perfume, colorants, insecticides, or humectants or combinations thereof. If the composition is used as a cosmetic, it may additionally include, for example, water, film forming materials, emulsifiers, softeners, emollients, oils, stabilizers, thickeners, preservatives, perfume, colorants, or pigments, or combinations thereof.

The composition improved by the method of this invention may be used in any application where protection from UV radiation is useful. For example, the improved composition may be used on human skin and hair, such as, for example personal care products, including, cosmetics, sunscreens, and hair care products. In addition, the method of this invention is also useful in improving the UV absorption and protection for coatings on plant life, plastics, wood, for example in the form of a clear varnish.

The method of this invention may be used to improve the UV radiation absorption in either clear or pigmented formulations. The method is particularly useful if a clear formulation is desired, such as a sunscreen formulation, because the addition of the voided latex particles having a particle size of less than about 300 nm does not significantly contribute to whiteness.

The method of this invention enables formulators to either increase the UV radiation absorbance of a given formulation or reduce the level of the UV radiation absorbing agent present in the formulation while maintaining a given UV radiation absorbance.

The compositions improved by the method of this invention may be applied to the skin at coating volumes, for example, of from about 0.5 microliters per square centimeter to about 4 microliters per square centimeter.

EXAMPLES

Some embodiments of the invention will now be described in detail in the following examples. The following abbreviations are used in the Examples:

| MMA | weight percent methyl methacrylate |
|---|---|
| BMA | weight percent butyl methacrylate |
| MAA | weight percent methacrylic acid |
| Sty | weight percent styrene |
| ALMA | weight percent allyl methacrylate |
| pbw | parts by weight |

For Examples 1 and 2, voided latex particles having particle sizes ranging from 150 nm to 548 nm were added to formulations containing at least one UV radiation absorbing agent to determine the effectiveness of the voided latex particles in improving the absorption of UV radiation.

The voided latex particles in Examples 1 and 2 were prepared similar to the method described in U.S. Pat. No. 4,427,836. The voided latex particles tested in Examples 1 and 2 had the following composition, unless stated otherwise:

Core: 1 pbw (60 MMA/40 MAA)
Shell 1: 16 pbw (10 BMA/86 MMA/4 MAA)
Shell II: 12 pbw (99.5 Sty/0.5 ALMA)
Shell III: 9 pbw (100 Sty)

To swell the core, excess ammonia (based on the total equivalents of acid in the monomer) was added to the hot (80°–85° C.) dispersion between the polymerization of shell II and shell III to swell the core. The voided latex particles had a final particle size and void fraction as shown in Table I.

The particle size of the voided latex particles was measured using a Brookhaven BI-90 photon correlation spectrometer.

The percent void fraction of the latex particles was measured by the centrifuge method described in the Detailed Description of the Invention.

TABLE 1

Voided Latex Particles for Examples 1 and 2

| Latex Particles | Particle Size (nm) | % Void Fraction |
|---|---|---|
| Polymer A | 150 | 11.3 |
| Polymer B | 160 | 10.0 |
| Polymer C | 249 | 23.5 |
| Polymer D | 263 | 28.3 |
| Polymer E | 282 | 28.3 |
| Polymer F | 400 | 36.5 |
| Polymer G | 548 | 30.5 |

Example 1

A composition containing voided latex particles useful in the present invention was evaluated for its effectiveness in absorbing UV radiation at varying coating thicknesses to simulate different levels of sunscreen on human skin. The composition containing the voided latex particles was also compared to a composition containing solid latex particles having a similar particle size to the voided latex particles. The following procedure was used:

Three compositions were prepared for UV radiation absorbance measurements:

| | |
|---|---|
| Comparative Composition A: | containing no voided latex particles or solid particles as additives (no additives) |
| Comparative Composition B: | containing solid polystyrene particles as an additive having a particle size of about 179 nm |
| Composition 1: | containing Polymer B as an additive (voided latex particles, see Table I) |

The compositions were prepared by adding the additive at a level of 5% solids, based on total weight solids, to Hawaiian Tropic Dark Tanning Lotion with an SPF of 4, manufactured by Tanning Research Laboratories. The UV absorbing materials in the Hawaiian Tropic Dark Tanning Lotion were 2-ethylhexyl para-methoxycinnamate and menthyl anthranilate.

The compositions prepared were coated at a level of 5, 10, 20 and 40 microliter per square inch ($\mu l/in^2$) on Transpore® tape from Minnesota Mining and Manufacturing Company to simulate different levels of sunscreen on human skin. The UV radiation absorbance spectra from a wavelength of 280–440 nm for each sample were measured using an Optronics Laboratories 752 Spectroradiometer. The spectra at coating levels of 5, 10, 20 and 40 $\mu l/in^2$ are shown in FIGS. 1, 2, 3 and 4, respectively.

Composition 1 containing both at least one UV radiation absorbing agent and voided latex particles exhibited increased UV radiation absorbance at each coating level over the wavelengths tested (280–440 nm) as compared to the composition containing only a UV radiation absorbing agent (Comparative Composition A). Composition 1 also exhibited increased UV radiation absorbance at each coating level as compared to Comparative composition B, containing a UV radiation absorbing agent and solid latex particles of a similar particle size to Polymer B. The results demonstrate that the presence of a void in the latex particles improves UV radiation absorbance of a composition containing a UV radiation absorbance agent.

Example 2

The voided latex particles useful in the present invention were evaluated for their effectiveness in absorbing UV radiation at varying particle sizes in a composition containing at least one UV absorbing agent. The procedure used was as follows:

A test composition containing the voided latex particles to be tested was prepared according to the composition shown in Table II (Test Composition).

TABLE II

| Test Composition | |
|---|---|
| Ingredient | Parts by Weight |
| Deionized water | 75.10 |
| Aculyn ® 22 | 2.25 |
| Triethanolamine 99% | 0.61 |
| Neo Heliopan Hydro (30%) | 12.00 |
| Kathon ® CG | 0.04 |
| Voided Latex Particles | 10.00 (as solids) |

A control composition, hereinafter referred to as "Control," was also prepared according to the composition shown in Table II, except that no voided latex particles were added. Aculyn®22, supplied by Rohm and Haas Company, was added to the composition to provide thickening. Kathon®CG, also supplied by Rohm and Haas Company was added to the test composition as a biocide. Neo Heliopan Hydro, a UV radiation absorbing agent, is supplied by Haarmann & Reimer and is chemically phenylbenzimidazole sulfonic acid.

The ability of the test composition to absorb UV radiation was evaluated by measuring the sun protection factor (SPF) of the test composition. The SPF was measured using an SPF 290 Analyzer and SPF Operating Software supplied by The Optometrics Group located in Ayer, Mass. The SPF 290 Analyzer measures the UV absorbance of a sample over UV radiation wavelengths and calculates an SPF value based on this UV absorbance spectrum. The following procedure for measuring SPF was used.

For each test composition, including the Control, a 10.16 cm long by 7.62 cm wide piece of Transpore® tape from Minnesota Mining and Manufacturing Company was cut and placed in the SPF 290 Analyzer. Using a 1.0 cc graduated syringe, 0.1 cc of the composition to be tested was evenly applied to a test area of about 50 square centimeter area. The composition was dried on the tape for 20 minutes.

While the composition to be tested was drying, a piece of tape containing no composition was measured for background UV absorbance using the SPF 290 Analyzer. The SPF 290 Analyzer subtracts the background absorbance of the tape to calculate the SPF for the test composition.

After drying, the test composition was measured for SPF using the SPF 290 Analyzer in 6 different locations within the test area of the tape. These 6 measurements were averaged together. The above procedure for measuring SPF was repeated for the same test composition, to obtain 6 additional SPF measurements. The 12 SPF measurements were averaged to obtain a final SPF.

TABLE III shows the Final SPF values for compositions which were tested according to the above procedure. Table III shows for each test composition, the latex particles which were tested, the particle size of the voided latex particles, the % void fraction of the latex particles, and the Final SPF value. A higher SPF value for a test composition indicates that a greater amount of UV radiation is being absorbed in comparison to another test composition having a lower SPF value. The data in TABLE III is also graphically shown in FIG. 5.

Figure 5:
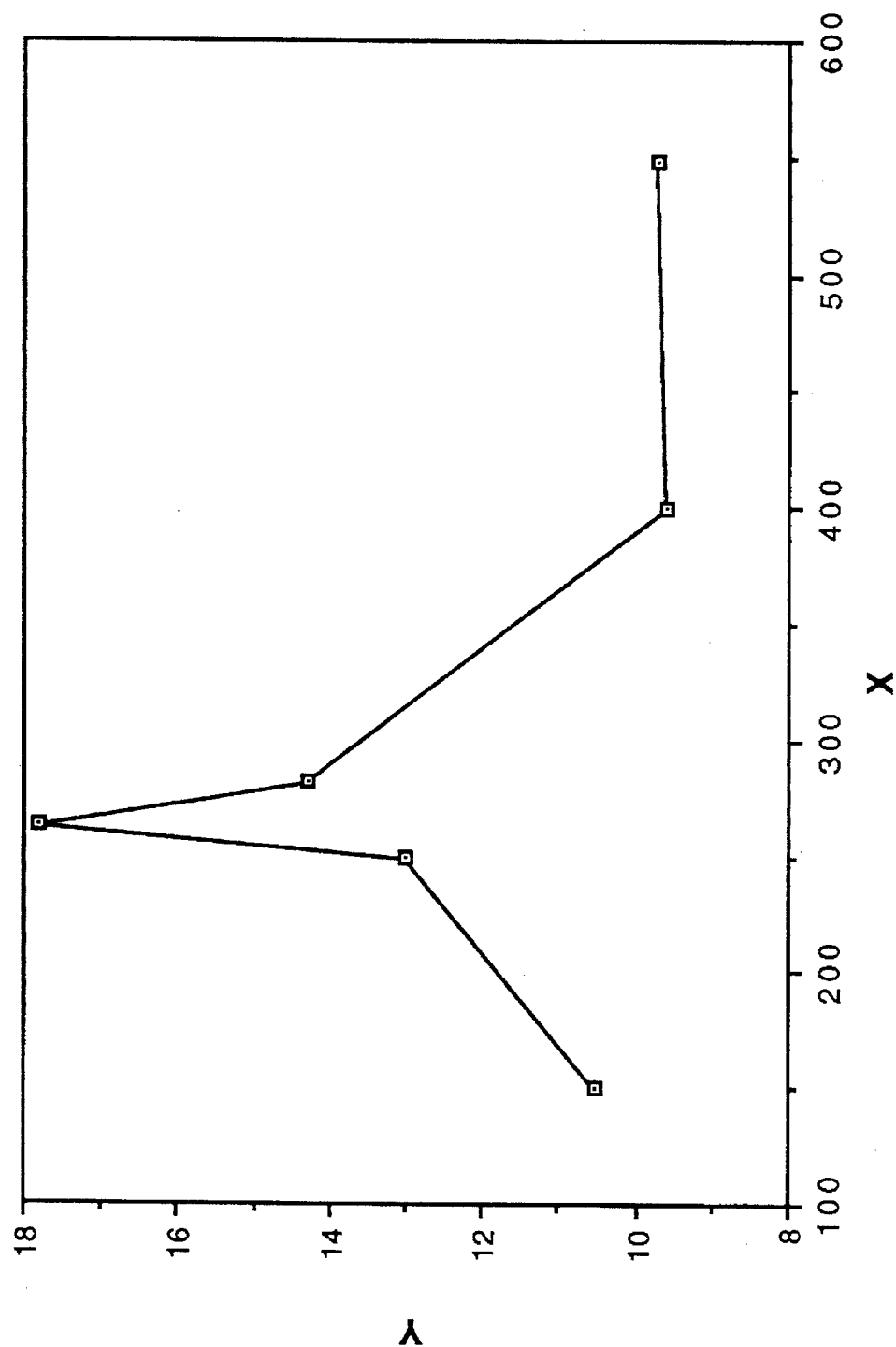
FIG. 5 is a graph showing for 6 UV radiation absorbing compositions, the relationship of the Sun Protection Factor (SPF) for the compositions (Y axis) versus the particle size, in nm, of voided latex particles contained in the compositions (X axis). The voided latex particles (as solids) are incorporated in the compositions at a level of 10 weight percent, based on total eight nonvolatiles. In addition to the voided latex particles, the compositions also contained, phenylbenzimidazole sulfonic acid, a UV radiation absorbing agent.

TABLE III and FIG. 5 show that the UV radiation absorbance of the test composition containing at least one UV radiation absorbing agent unexpectedly increases when the voided latex particles have a particle size of from about 100 nm to about 380 nm. The increase is especially great within the particle size range of from about 190 nm to about 350 nm.

TABLE III

Final SPF Values for Test Compositions Containing Voided Latex Particles

| Composition Measured | Latex Particles Tested | Particle Size (nm) | % Void Fraction | Final SPF |
|---|---|---|---|---|
| Control | None | — | — | 1.3 |
| Test composition 1 | Polymer A | 150 | 11.3 | 10.5 |
| Test composition 2 | Polymer C** | 249 | 23.5 | 13.0 |
| Test composition 3 | Polymer D** | 263 | 28.3 | 17.8 |
| Test composition 4 | Polymer E** | 282 | 28.3 | 14.3 |

TABLE III-continued

Final SPF Values for Test Compositions Containing Voided Latex Particles

| Composition Measured | Latex Particles Tested | Particle Size (nm) | % Void Fraction | Final SPF |
|---|---|---|---|---|
| Test composition 5* | Polymer F** | 400 | 36.5 | 9.6 |
| Test composition 6* | Polymer G** | 548 | 30.5 | 9.7 |

*comparative
**Polymers C, D, E, F, and G were compositionally similar to polymer A.

We claim:

1. A method for improving UV radiation absorption of a composition, comprising: adding to said composition from about 0.1 weight percent to about 50 weight percent of latex particles, based on total weight nonvolatiles, wherein the composition comprises at least one UV radiation absorbing agent, wherein the latex particles contain a void and have a particle size of from about 100 nm to about 380 nm, and wherein the latex particles are added to increase the UV radiation absorption of the composition.

2. The method of claim 1, wherein the latex particles are added to said composition to provide a level from about 1.0 weight percent to about 20 weight percent of the latex particles in said composition.

3. The method of claim 1, wherein the particle size of the latex particles is from about 150 nm to about 375 nm.

4. The method of claim 1, wherein the particle size of the latex particles is from about 190 nm to about 350 nm.

5. The method of claim 1 wherein the latex particles have a void fraction of from about 0.1% to about 50%.

6. The method of claim 1 wherein the latex particles have a void fraction of from about 5% to about 50%.

7. The method of claim 1 wherein the UV radiation absorbing agent is a chemical selected from the group consisting of oxybenzone, dioxybenzone, sulisobenzone, menthyl anthranilate, para-aminobenzoic acid, amyl para-dimethylaminobenzoic acid, octyl para-dimethylaminobenzoate, ethyl 4-bis (hydroxypropyl) para-aminobenzoate, polyethylene glycol (PEG-25) para-aminobenzoate, ethyl 4-bis (hydroxypropyl) aminobenzoate, diethanolamine para-methyoxycinnamate, 2-ethoxyethyl para-methoxycinnamate, ethylhexyl para-methoxycinnamate, octyl paramethoxycinnamate, isoamyl para-methoxycinnamate, 2-ethylhexyl 2-cyano-3,3-diphenyl-acrylate, 2-ethylhexyl salicylate, homomenthyl salicylate, glyceryl aminobenzoate, triethanolamine salicylate, digalloyl trioleate, lawsone with dihydroxyacetone, 2-phenylbenzimidazole-5-sulfonic acid, benzylidine camphor, avobenzone, titanium dioxide and zinc oxide.

* * * * *